US 6,183,517 B1

(12) United States Patent
Suddaby (10) Patent No.: US 6,183,517 B1
(45) Date of Patent: Feb. 6, 2001

(54) EXPANDABLE INTERVERTEBRAL FUSION IMPLANT AND APPLICATOR (76) Inventor: Loubert Suddaby, 76 Tanglewood Dr., Orchard Park, NY (US) 14127

( * ) Notice: Under 35 U.S.C. 154(b), the term of this patent shall be extended for 0 days.

(21) Appl. No.: 09/212,288

(22) Filed: Dec. 16, 1998

(51) Int. Cl.$^7$ ...................................................... A61F 2/44
(52) U.S. Cl. ......................................................... 623/17.16
(58) Field of Search .................................. 623/17, 17.11, 623/17.12, 17.13, 17.15, 17.16

(56) References Cited

U.S. PATENT DOCUMENTS

| 4,863,476 | * | 9/1989 | Shepperd ................................ 623/17 |
| 5,483,463 | | 1/1996 | Qin et al. . |
| 5,505,732 | | 4/1996 | Michelson . |
| 5,653,762 | | 8/1997 | Pisharodi . |
| 5,665,122 | * | 9/1997 | Kambin ................................... 623/17 |
| 5,683,462 | | 11/1997 | Godefroy et al. . |
| 5,888,228 | * | 3/1999 | Knothe et al. .......................... 623/17 |
| 5,928,284 | * | 7/1999 | Mehdizadeh ............................ 623/17 |
| 5,980,522 | * | 11/1999 | Koros et al. ............................. 606/61 |
| 6,019,792 | * | 1/2000 | Cauthen .................................. 623/17 |
| 6,019,793 | * | 2/2000 | Perren et al. ........................... 623/17 |

* cited by examiner

Primary Examiner—V. Millin
Assistant Examiner—Alvin Stewart
(74) Attorney, Agent, or Firm—Shoemaker and Mattare (57) ABSTRACT An expandable intervertebral fusion implant includes a pair of semi-cylindrical shells having mating surfaces which resist shifting when the parts are assembled. The cylinder thus formed is placed on a special installation tool, which is first used to place the cylinder in the intervertebral space. Thereafter, the tool is actuated to spread the shells, and a spacer of appropriate size and taper is slid over the tool shaft, and in between the shells to maintain their spacing after the tool is removed. Having spacers of different height and taper allow the surgeon to adapt the implant to various situations.

3 Claims, 10 Drawing Sheets

EXPANDABLE INTERVERTEBRAL FUSION IMPLANT AND APPLICATOR

BACKGROUND OF THE INVENTION

This invention relates to an expandable intervertebral fusion implant and applicator. The class of implements to which this invention pertains serve to stabilize adjacent vertebral elements, thereby facilitating the development of a bony union between them and thus long term spinal stability.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures—discs—composed of fibrous tissue and cartilage which are compressible and act as shock absorbers for sudden downward forces on the upright column. The discs allow the bones to move independently of each other, as well. The repetitive forces which act on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, may spinal surgeons have found that interbody fusion using bone alone has an unacceptably high rate of bone graft migration or even expulsion or nonunion due to structural failure of the bone or residual degrees of motion that retard or prohibit bony union. Intervertebral prostheses in various forms have therefore been used to provide immediate stability and to protect and preserve an environment that fosters growth of grafted bone such that a structurally significant bony fusion can occur.

U.S. Pat. No. 5,505,732, No. 5,653,762, No. 5,665,122, and No. 5,683,463 describe different prior spinal implants. The implant shown in U.S. Pat. No. 5,483,463 is hollow and tubular, with communicating windows in the top and bottom surfaces. External ribs, which may be serrated, stabilize the implant once it is inserted between the vertebrae. In U.S. Pat. No. 5,665,122, an intervertebral cage is rendered expandable by a wedging mechanism. The degree of expansion is rather limited, however. U.S. Pat. Nos. 5,653,762 and 5,505,732 show shaft-type tools used for installing implants. The prior devices do not enable one to achieve great ranges of implant height, or to adjust taper angle for kyphotic and lordotic situations. Limitations of most present-day intervertebral implants are significant and revolve largely around the marked variation in disc space shape and height that results from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2–3 mm must be added on either end, resulting in a final implant size of 24–26 mm. During implantation from an anterior approach (from the front of the body), excessive retraction (pulling) is often required on the great blood vessels which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of ligamentous laxity requiring higher degrees of distraction to obtain stability by tautening the annular ligamentous tension band. Compromising on implant size risks sub-optimal stability or a loose implant, which has a greater chance for migration within or expulsion from the disc space. The alternative of excessively retracting neural elements to facilitate a posterior implant application results in a neuropraxia at best and permanent neural damage at worst.

SUMMARY OF THE INVENTION

It is the object of this invention to provide an expandable intervertebral fusion implant that is both simple to manufacture and simple to use in daily clinical surgical practice while remaining versatile enough to address the complex biologic and pathologic variability of the human spine.

It is also intended that this device be applicable to all generally accepted surgical approaches to the spine, including microsurgical and endoscopic applications.

To achieve these objectives, a pair of semicylindrical shells are distracted inside an intervertebral space that has been appropriately prepared for fission. An expansible installation tool is used to achieve optimal distraction, and then a spacer having the desirable height and neutral, kyphotic or lordotic attitude is slid over the installation tool, thereby filling the gap between the shells. The installation tool is then unscrewed and disengaged, leaving the component parts as a stable assembly that can be packed with bone to promote osseous union.

The present invention not only provides an expandable intervertebral fusion implant, but also lends itself readily to use in anterior, lateral and posterior approaches. Providing tapered spacers with neutral, lordotic or kyphotic attitudes means that the broad spectrum of variability in the human spine can be more adequately addressed from a biomechanical point of view. In addition, one can insert devices of different sizes in a single intervertebral space to address lateral differences in disc space height to account for degrees of scoliosis, or lateral spinal curvature.

The cylindrical implant is split horizontally so that the cranial (upper) and caudal (lower) shells that contact the vertebral bones above and below can be distracted, or spread apart, by a screw-type installation tool until optimal distraction of the vertebral elements and appropriate tension on the ligamentous structures is achieved. Then, a spacer having a desired thickness and taper is slid over the screw implanted to fill the gap between the shells. The installation tool is then retracted, allowing the three components to seat against one another and lock together, and the tool is then removed. The implant assembly is now packed with allograft or auto graft bone to allow long term bony union to develop between the vertebral elements.

The advantages provided by this invention include (1) the fact that both the tool and the implant components are of simple manufacture, and (2) by providing the surgeon with a variety of spacers, he or she can construct implants of the proper size and shape for a variety of situations. Indeed, because of its expandable nature, this implant has the potential for use in microsurgical laminotomy, where only a small opening is made in the spine, resulting in minimal retraction of neural structures and maximizing preservation of posterior bony and ligaments spinal elements. Most existing posterior interbody approaches require extensive bone removal to achieve spinal fusion whether or not an implant is used.

BRIEF DESCRIPTION OF THE DRAWINGS

In the accompanying drawings,

FIG. 3a is an unexploded front elevation.

DESCRIPTION OF THE PREFERRED EMBODIMENT

An expandable intervertebral fusion implant embodying the invention appears in FIGS. 1–5. The implant in every case comprises a pair of semicylindrical shells 10, 12, and, in most cases, a spacer 40 having angularity and height selected to provide the desired effective height and shape of the implant assembly. The shells have complementary mating surfaces, one having vee-profile ridges 14 and the other having vee-grooves 16 for preventing the parts from shifting laterally. One end of each half-shell is closed by an end wall 20 having a vee-shaped ridge 22 on its diametral edge 24. The other half-shell also has one end wall, this having a vee-groove 26 shaped to receive the beveled edge of its counterpart. When assembled, the nesting edges of the end walls prevent longitudinal shifting of the parts.

Figure 1:
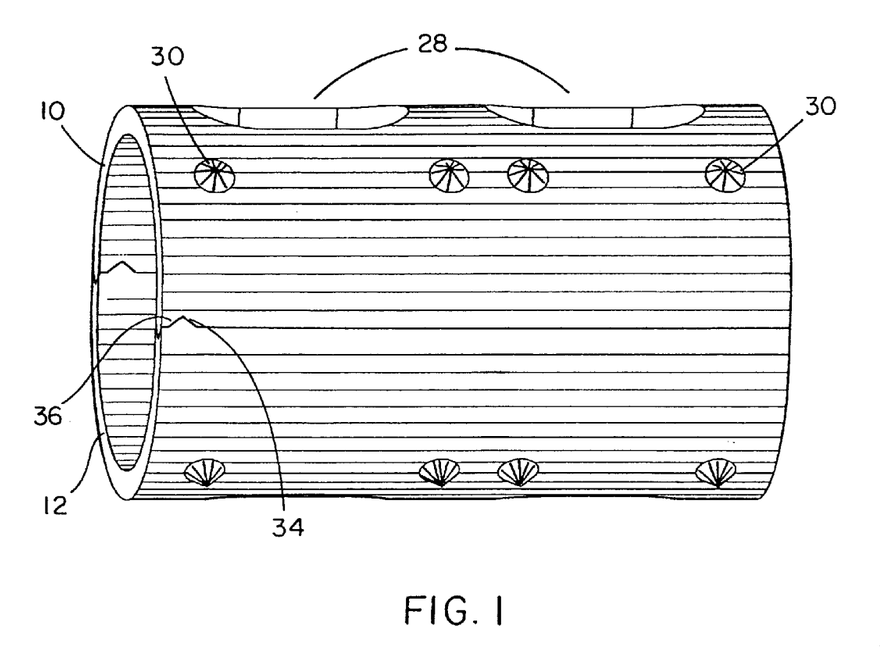
FIG. 1 is perspective view, from the side, of an expandable intervertebral fusion implant embodying the invention.

Each shell preferably has one or two windows 28 to encourage bone growth. The points 30 adjacent the windows dig into the surfaces of the bones between which the implant is installed.

The longitudinal surfaces of the shells also are interrupted by complementary structures such as a detent 32 on one shell and a protrusion 34 on its mate, to keep the parts from moving lengthwise once the spacer has been installed and the nesting diametral edges of the end walls are no longer in contact to perform this function.

Figure 2:
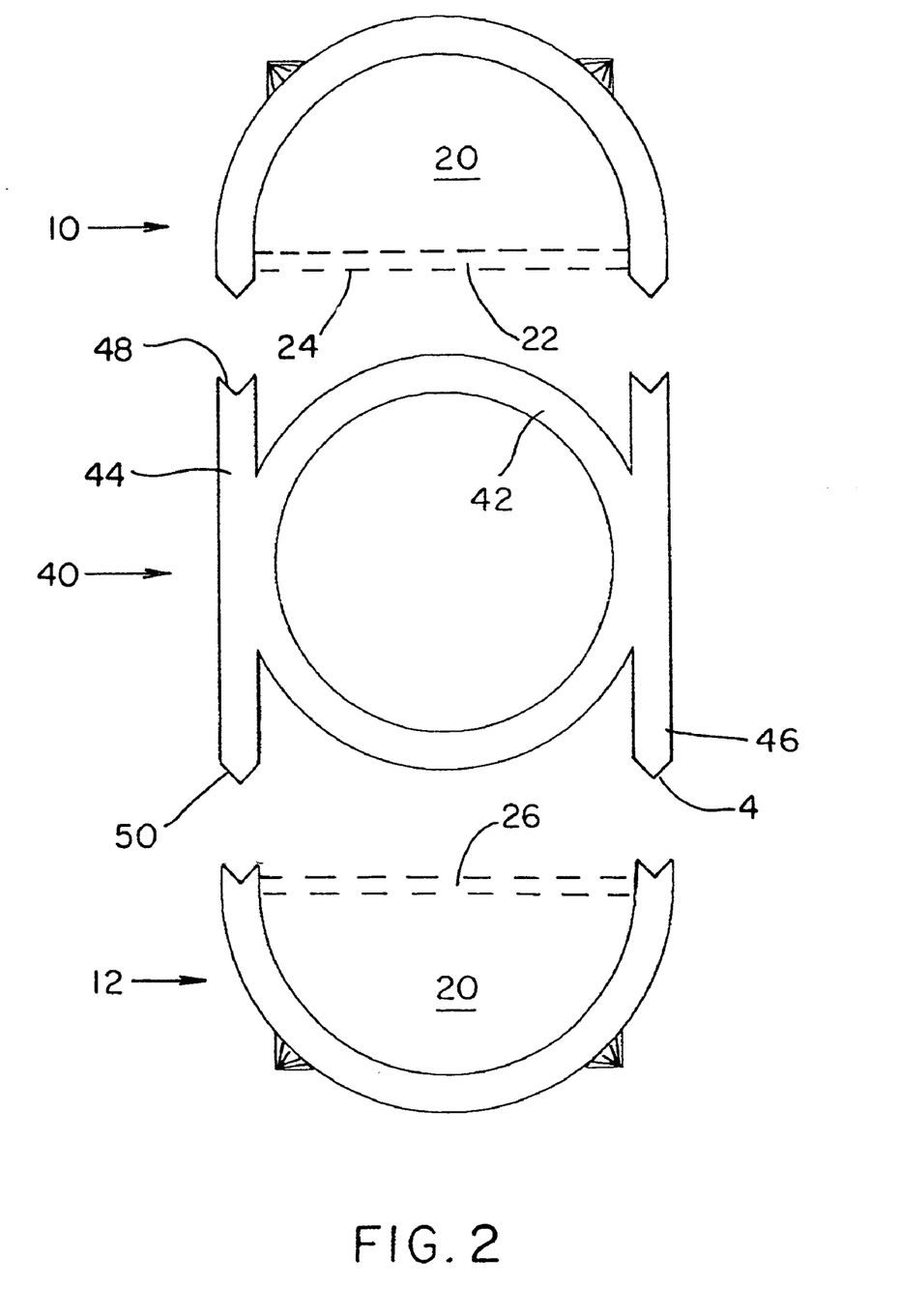
FIG. 2 is an exploded front elevation thereof, with a spacer added.
Figure 3A:
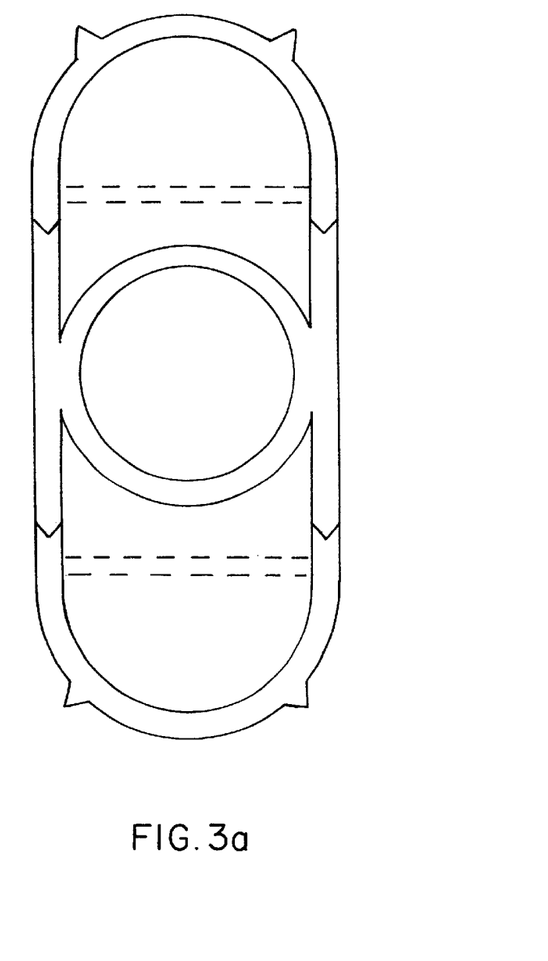
Figure 3B:
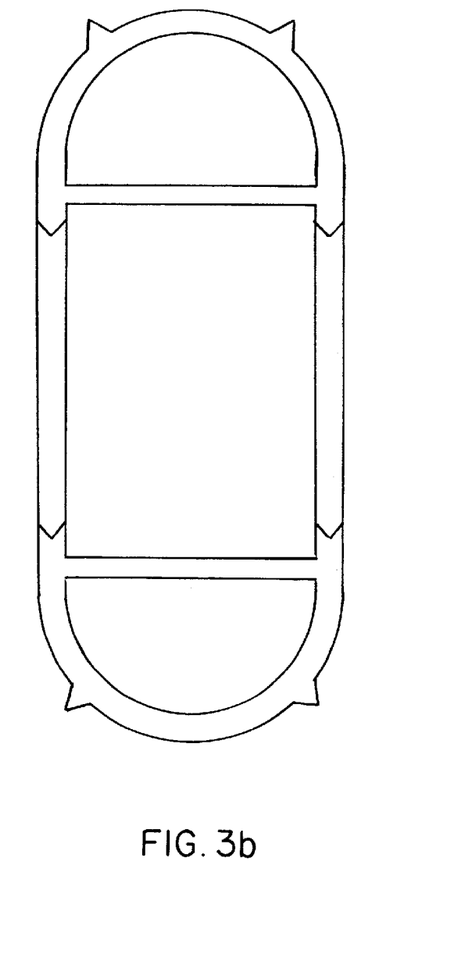
FIG. 3b is a corresponding rear elevation, of the implant.
Figure 4:
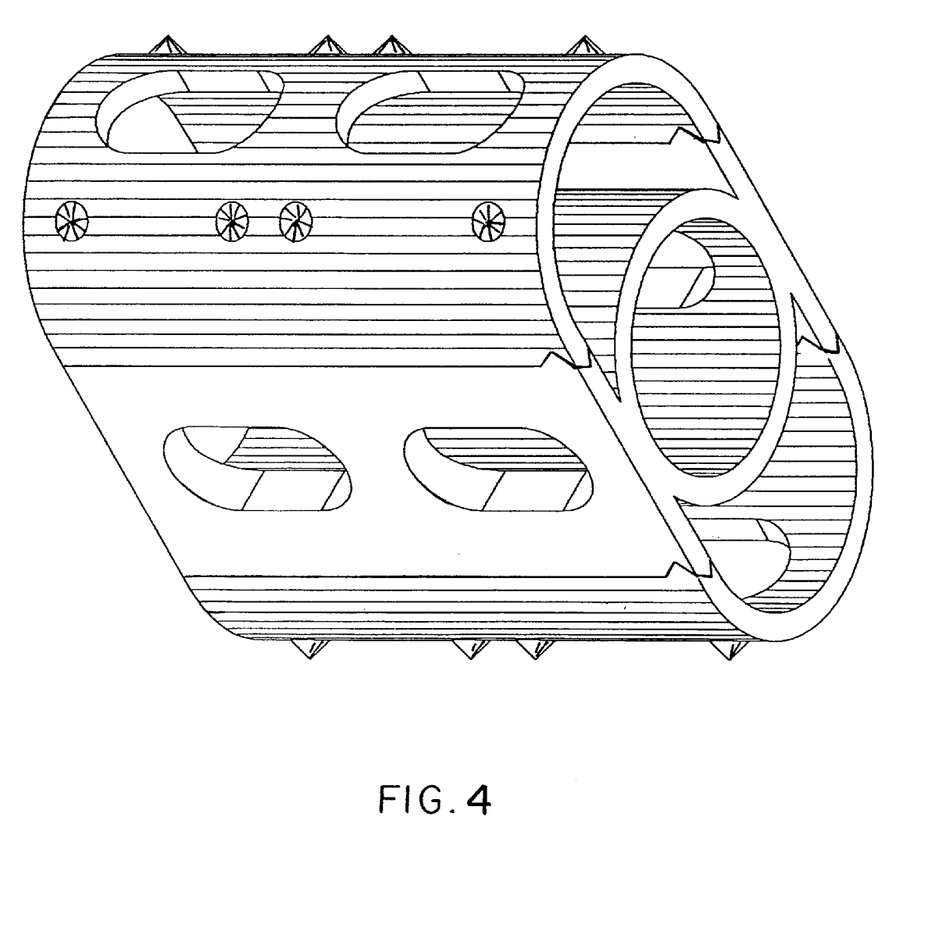
FIG. 4 is a perspective view showing the spacer locked in place.

FIG. 2 shows the two shells exploded away from another, exaggerating the distraction which is produced during installation. The spacer 40 between the shells has a profile like the capital Greek letter omega, featuring a cylindrical center portion 42 between two parallel side plates 44,46. The free edges 48,50 of the side plates have complementary vee-profiles, to prevent lateral shifting of the parts, as described before. FIGS. 3a and 3b show the parts assembled, as seen from the front and the rear, respectively. The isometric view (FIG. 4) reveals a pair of windows 52,54 in one side wall of the spacer, similar to those in the shells. The spacer, being symmetrical, has windows in its other wall as well.

Figure 5A:
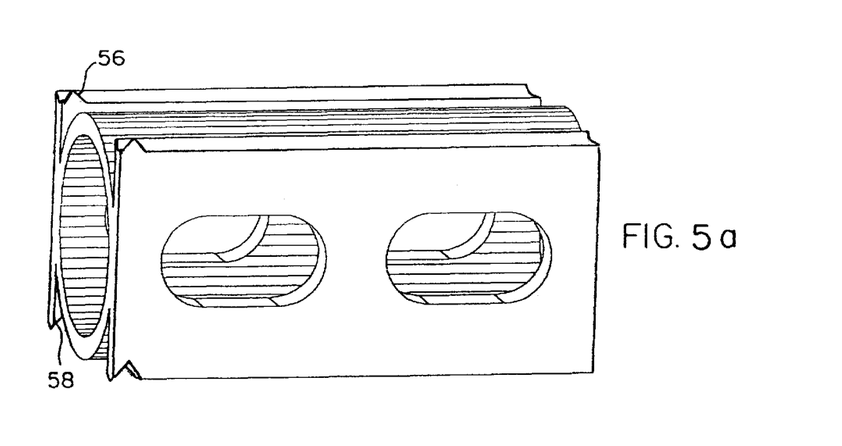
FIG. 5a–5c show alternative spacers having, respectively, neutral, lordotic and kyphotic tapers.
Figure 5B:
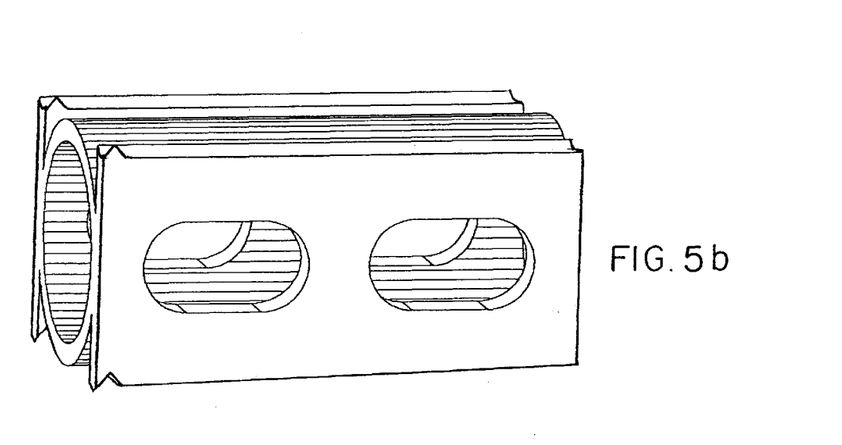
Figure 5C:
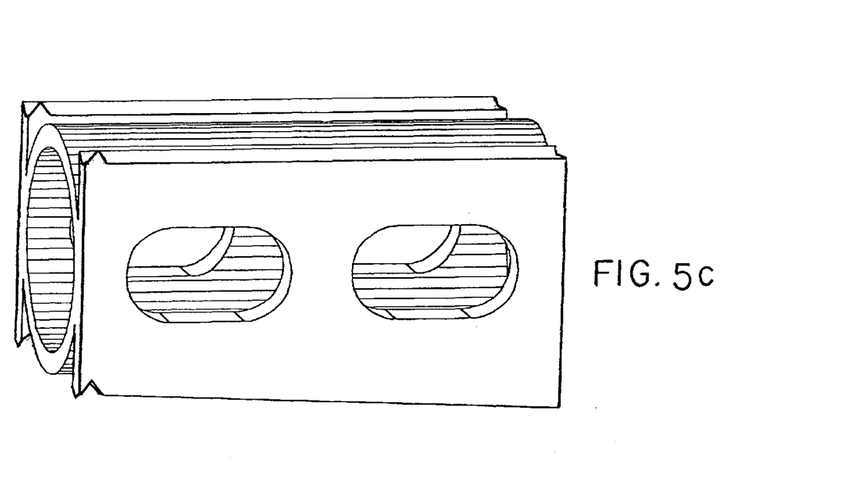

The spacers shown in FIGS. 5a–5c differ in their longitudinal taper. In 5a, there is no taper; in 5b, the taper is front-to-rear (lordotic), and in 5c, the taper is rear-to-front (kyphotic). The protrusions 56 and detents 58 mark the front of the spacer.

The spacers and the shells may be made of the same material, or different materials. Suitable materials include stainless steel, titanium, ceramic, graphite, and various plastics and composites of the foregoing. The selection of material may affect the dimensions or proportions of the parts somewhat, but is generally a matter of design choice.

Figure 6:
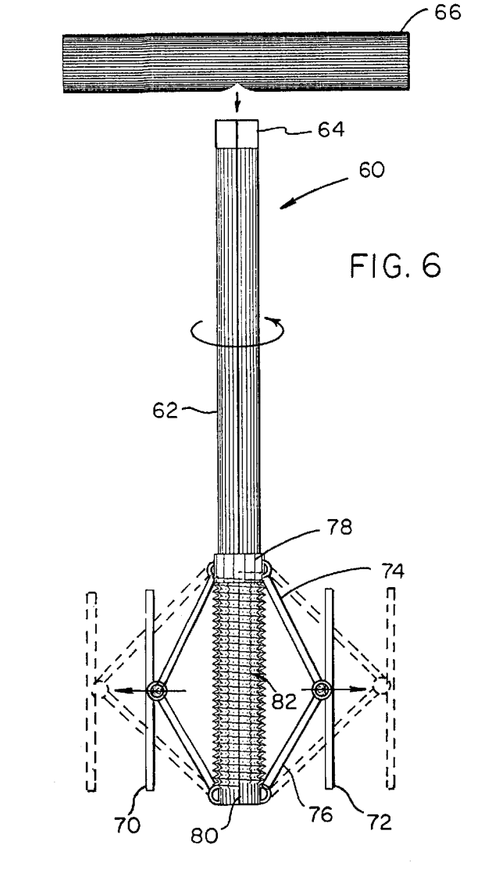
FIG. 6 is a side view of a tool for installing the implant, in a partially retracted mode.
Figure 7:
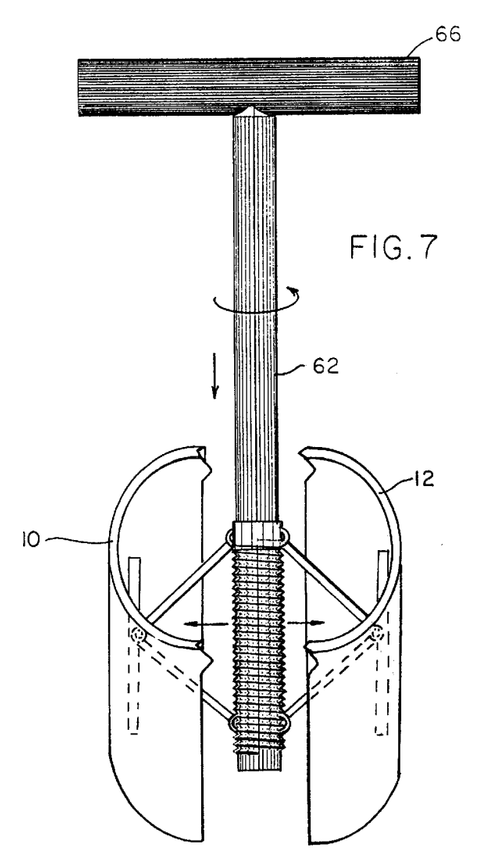
FIG. 7 is a view like FIG. 7, showing the tool in a deployed mode.
Figure 8:
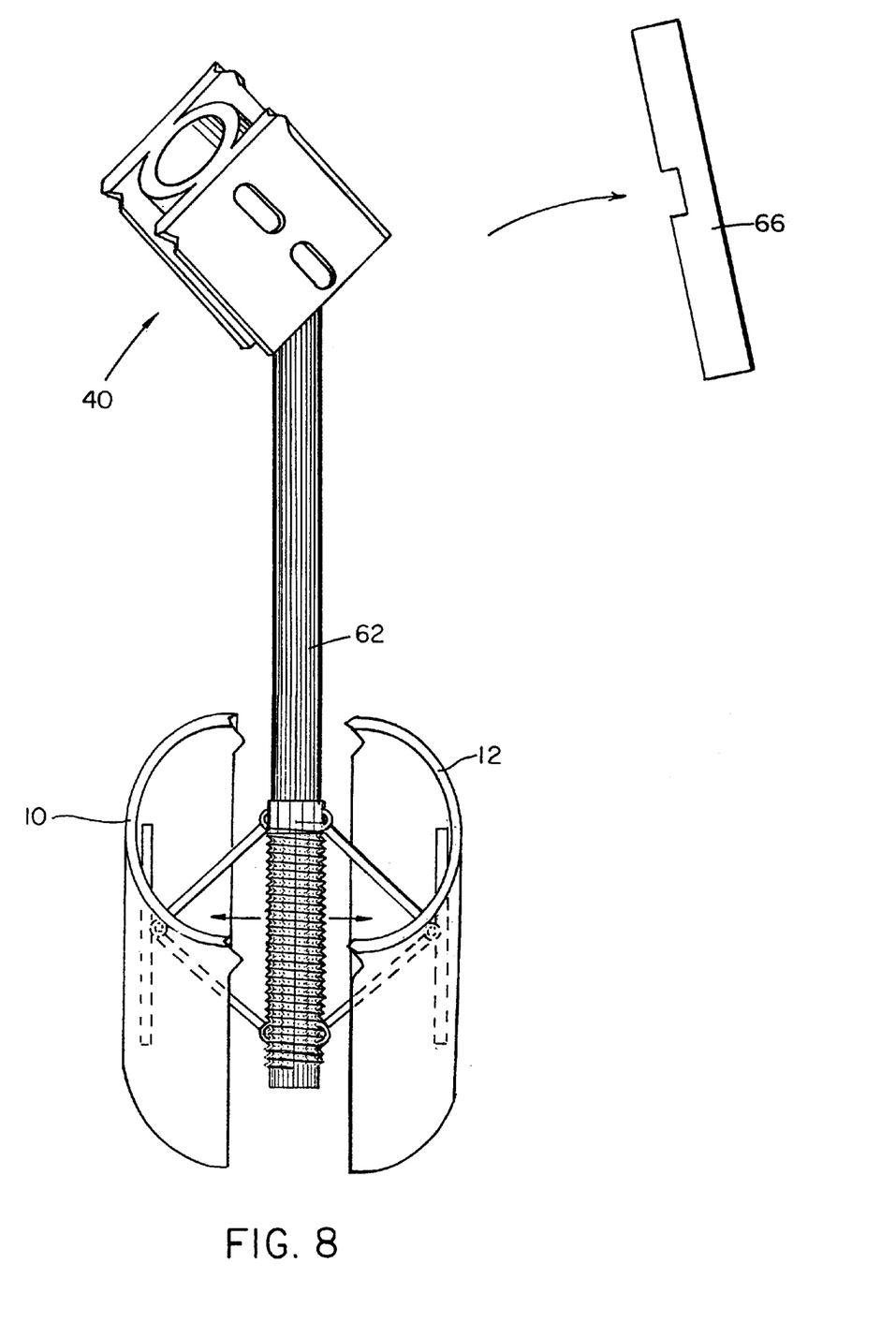
FIG. 8 shows the handle of the tool having been removed, and a spacer as in FIG. 5a being installed over the tool's shaft.
Figure 9:
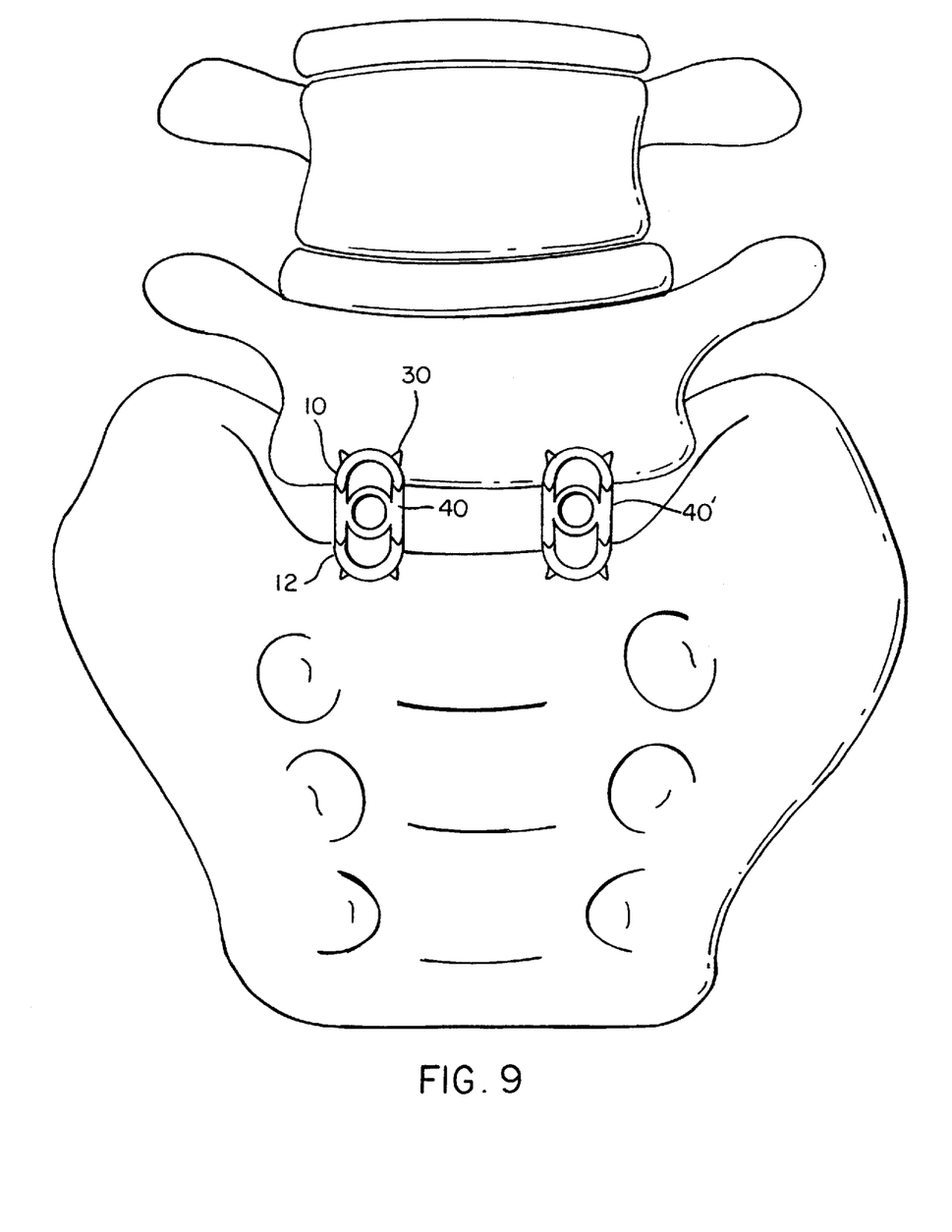
FIG. 9 is a posterior view of a pair of implants in position between the pelvis and a lumbar element.
Figure 10:
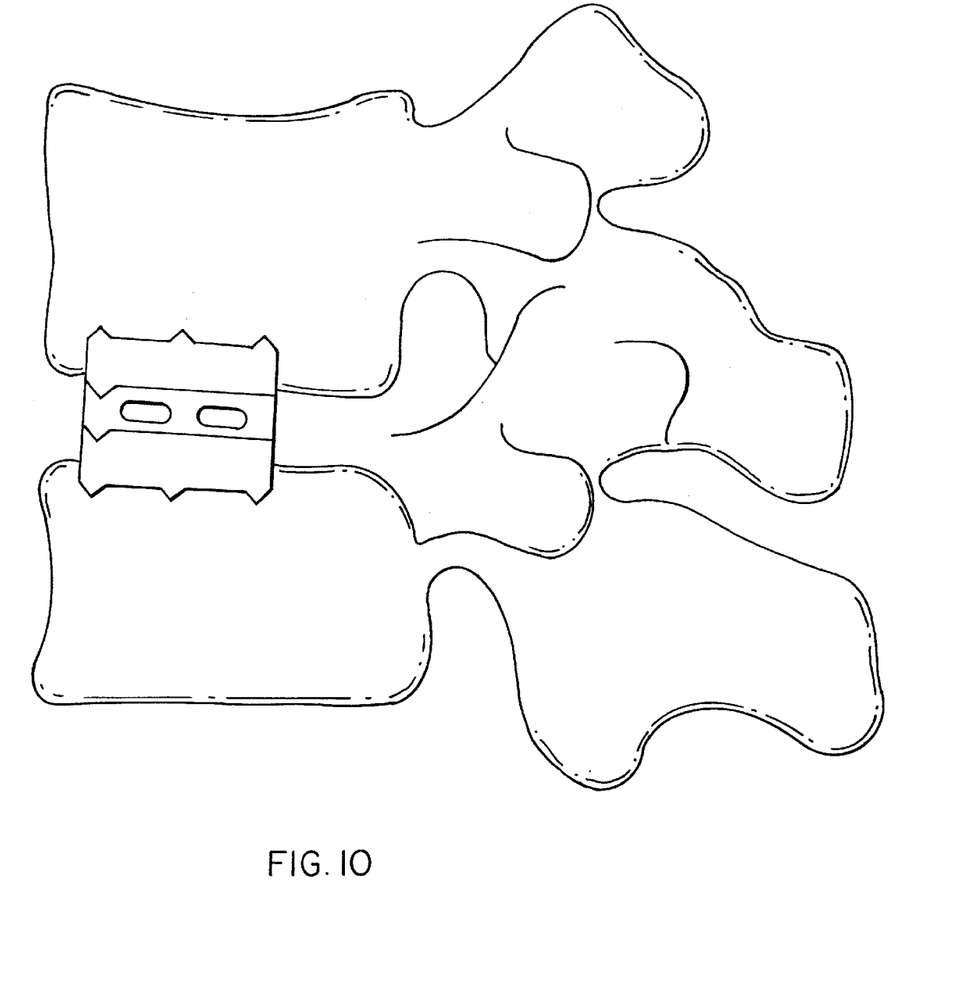
FIG. 10 is a side view of an implant installed between two vertebrae.
Figure 11:
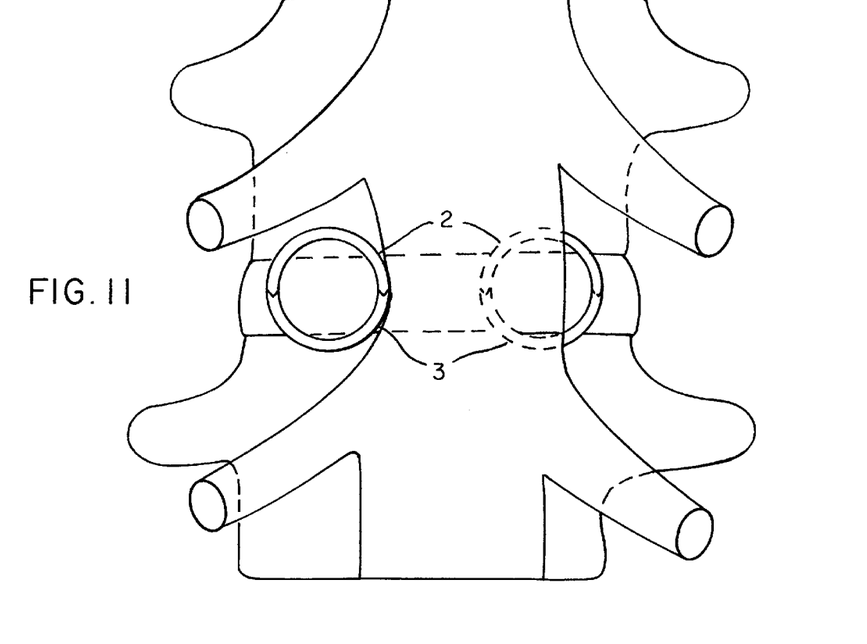
FIG. 11 is an anterior view of a pair of implants installed between two vertebrae, without spacers.
Figure 12:
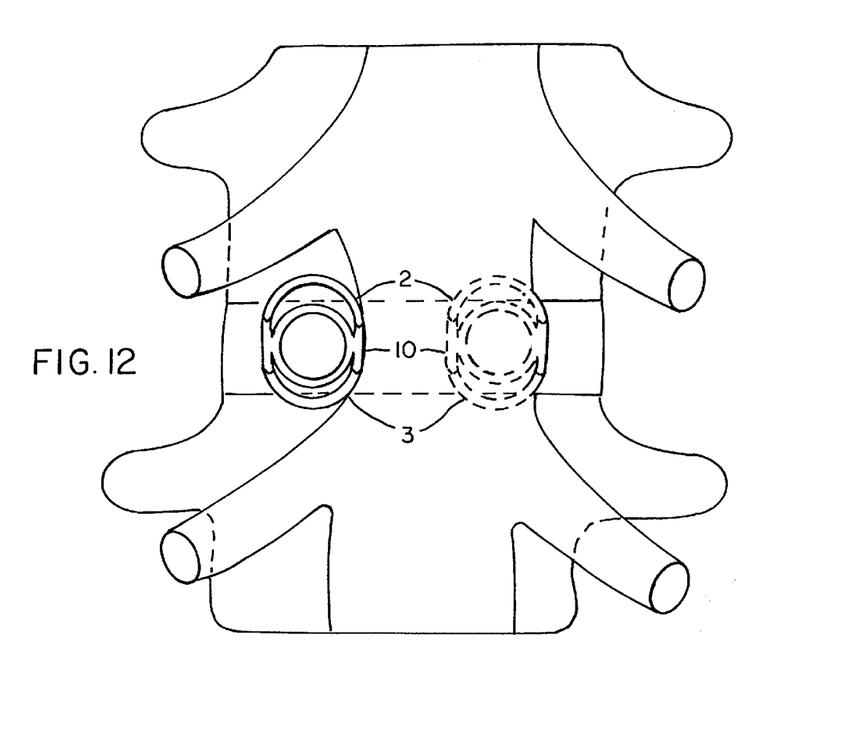
FIG. 12 is a similar view, showing spacers which have been added.

The installation tool 60 is shown in FIGS. 6–8. In general, it includes a shaft 62 having one non-circular end 64 for receiving a removable handle 66. The other end has a radially expandable structure 68, preferably in the form of two jaws 70,72, each of which is connected at its midpoint to the outer ends of a pair of pivoting arms 74,76. The inner ends of these arms are hinged to respective collars 78,80 or the like at the ends of a screw thread 82 on the shaft. The screw mechanism changes the spacing between the collars as the handle is rotated, thus driving the jaws in (FIG. 6) or out (FIG. 7).

To install an implant, the shells are assembled and placed in the selected empty intervertebral space by means of the tool, with its jaws retracted, and aligned with the spine. Then the jaws are spread but turning the handle clockwise, forcing the shells outward into contact with the bones above and below. The points on the shells dig into the bony material somewhat.

FIG. 8 shows the jaws still distended. The handle 66 has been removed as suggested by the arrow, one spacer 40 now being passed over the handle end of the tool. The spacer is down the shaft, toward the jaws, until it lies partially in between the shells. The handle is then reinstalled on the tool, and turned counterclockwise to retract the jaws. With the jaws retracted, the tool can be removed from the site, and finally the spacer is pushed fully between the shells until the protrusions and detents seat, locking the assembly together.

FIGS. 9–12 show how two implants 40,40' of different height can be placed in an intervertebral space to compensate for or conform to lateral deviations of the spine. Such elements are useful in filling correspondingly tapered spaces which occur, for example, in the lumbar region, and account for the curvature of the spine. A number of spacers, having different thicknesses and taper angles, may be provided to accommodate different situations.

Since the invention is subject to modifications and variations, it is intended that the foregoing description and the accompanying drawings shall be interpreted as only illustrative of the invention defined by the following claims.

I claim:

1. An expandable intervertebral fusion implant comprising a pair of shells having mating surfaces so that when joined, the shells form substantially a tube, said mating surfaces having complementary profiles to prevent lateral and longitudinal shifting of the shells with respect to one another once they are assembled, a spacer for placement between the shells, once they have been positioned in an intervertebral space, so as to give the spacer a predetermined total height appropriate for the intervertebral space, said spacer having mating surfaces complementary to those of the shells, wherein the spacer comprises a pair of parallel walls interconnected by an cylindrical center portion having a longitudinal through hole.

2. The invention of claim 1, wherein the longitudinal hole has an internal diameter substantially the same as that of said tube.

3. The invention of claim 1, wherein each of said shells has one end wall, said end walls having mating edges provided with complementary nesting profiles to prevent longitudinal shifting of said shells.

* * * * *